US006670074B2

United States Patent
Spillman

(10) Patent No.: US 6,670,074 B2
(45) Date of Patent: Dec. 30, 2003

(54) GLASS TO METAL SEAL

(75) Inventor: David M. Spillman, Tonawanda, NY (US)

(73) Assignee: Wilson Greatbatch Ltd., Clarence, NY (US)

( * ) Notice: Subject to any disclaimer, the term of this patent is extended or adjusted under 35 U.S.C. 154(b) by 360 days.

(21) Appl. No.: 09/840,674

(22) Filed: Apr. 23, 2001

(65) Prior Publication Data

US 2002/0155350 A1 Oct. 24, 2002

(51) Int. Cl.[7] ................................................ H01M 6/16
(52) U.S. Cl. ........................ 429/181; 429/178; 429/185
(58) Field of Search ......................... 429/65, 178, 179, 429/180, 181, 185, 231.95

(56) References Cited

U.S. PATENT DOCUMENTS

| 4,465,743 A | * | 8/1984 | Skarstad et al. ............ 429/105 |
|---|---|---|---|
| 5,434,017 A | | 7/1995 | Berkowitz et al. ............ 429/94 |
| 5,658,688 A | | 8/1997 | Jolson ........................ 429/194 |
| 5,709,724 A | | 1/1998 | Naugler et al. ............... 65/59.4 |
| 5,727,313 A | | 3/1998 | Paterek et al. ................ 29/877 |
| 5,871,513 A | | 2/1999 | Taylor et al. ................. 607/36 |
| 5,935,728 A | * | 8/1999 | Spillman et al. ............... 429/94 |
| 6,076,017 A | | 6/2000 | Taylor et al. ................. 607/36 |
| 6,090,503 A | * | 7/2000 | Taylor et al. ............... 429/181 |
| 6,440,603 B1 | * | 8/2002 | Heller, Jr. .................... 429/209 |
| 2001/0016280 A1 | * | 8/2001 | Probst et al. ................ 429/175 |

\* cited by examiner

Primary Examiner—Randy Gulakowski
Assistant Examiner—Monique Wills
(74) Attorney, Agent, or Firm—Michael F. Scalise

(57) ABSTRACT

It has been discovered that the connection between a current collector and a molybdenum terminal pin can be improved by roughening the terminal pin. However, a roughened terminal pin detracts from the integrity of the glass-to-metal seal. To overcome this, a sleeve or couple surrounds that portion of the roughened terminal pin that will be sealed to the insulating glass. The sleeve or couple is welded at each end to the terminal pin, and a glass-to-metal seal is formed between the sleeved terminal pin, the insulating glass, and the metallic lid. The resulting assembly contains a portion of the terminal pin that has a roughened surface and is suitable for making a high strength connection to a current collector of a primary or secondary lithium ion battery.

20 Claims, 6 Drawing Sheets

GLASS TO METAL SEAL

BACKGROUND OF THE INVENTION

1. Field of the Invention

The invention pertains to a glass-to-metal seal that is suitable for hermetically sealing an electrochemical cell. The glass-to-metal seal includes a terminal pin that is roughened to enhance its high strength connection to a current collector. The problem is that while a roughened terminal pin improves the current collector connection, it detracts from the hermetic seal with the glass of the glass-to-metal seal. According to the present invention, this is overcome by passing the terminal pin through a sleeve, and the two are hermetically sealed together. The sleeve then provides the seal for the glass-to-metal seal. Cells having the sleeved/roughened terminal pin assembly are adaptable for powering a number of devices including medical applications such as a pacemaker, cardioventer defibrillator, drug pump, hearing assist device or neurostimulator.

2. Prior Art

The recent rapid development in small-sized electronic devices having various shape and size requirements necessitates comparably small-sized electrochemical cells of different designs that can be easily manufactured and used in these devices. Preferably, the electrochemical cell has a high energy density and one commonly used cell configuration is a prismatic, case-negative cell design having an intermediate cathode flanked by, and in electrical association with, opposed anode plates in contact with the casing. In conjunction with smaller size batteries, enhanced characteristics such as a novel glass-to-metal seal which is suitable for hermetically sealing an electrochemical cell as well as providing a high strength connection to a current collector, will increase the applicability of these cells to an increasing number of situations. As will be seen shortly, the prior art does not teach the use of a metal sleeve to be used in conjunction with a roughened terminal pin.

For example, the prior art in U.S. Pat. No. 5,727,313 to Paterek et al. shows a method of manufacturing vessel lid covers including conductive pin assemblies for vessel container housings. The conductive pin and vessel lid cover are plated to reduce corrosion. However, the plating is removed from the aperture receiving the pin. The assembled lid cover is then heated to fuse the fusible insulative material to the peripheral wall of the pin and the inner face of the aperture wall where the plating has been substantially removed so as to enhance the fusing step. This invention does not teach the use of a sleeve in conjunction with the conductive pin as stated in the current invention. In contrast, the invention teaches a cumbersome construction which is expensive and difficult to manufacture.

U.S. Pat. No. 6,076,017 to Taylor et al. relates to a method for forming a glass-metal hermetic seal between a metal pin and a sealing glass wherein the pin may be of molybdenum, tantalum, niobium or similar metals. The surface of the pin is subjected to a centerless grinding process for removing defects and anomalies before being circumferentially and sealingly engaged with the sealing glass. A similar method is utilized in U.S. Pat. No. 5,871,513, also to Taylor et al. This invention teaches the smoothing of a larger pin in contrast to the current invention which teaches roughening of the pin surface connected to an electrode current collector.

Also, U.S. Pat. No. 5,709,724 to Naugler et al. shows a process for fabricating a hermetic glass-to-metal seal between a conductive pin, a glass, and an outer body. The process generally includes the steps of providing a conductive pin having a layer of noble metal coated on at least a portion of its outer surface, placing glass having a softening point of less than about 650° C. within the cavity of an outer body, inserting the coated pin into the glass, heating the components to a temperature at least equal to the softening point of the glass and less than about 700° C., and cooling the components to solidify the glass and form a glass-to-metal seal. This invention teaches the use of a noble metal such as gold or platinum in contrast to the current invention which uses a titanium, stainless steel, or molybdenum pin. This patent also does not teach the use of a sleeve provided on the pin intermediate the sealing glass.

Finally, U.S. Pat. No. 5,658,688 to Jolson teaches a battery having an austenitic stainless steel case and a cover blank. The cover blank is provided with a small hole allowing a glass-to-metal seal to be fused to the cover blank. A metal feedthrough pin is provided and is surrounded and held in place by an insulator preferably made of Fusite 435 glass. Rather than using TA-23 or CABAL glasses which require the use of a molybdenum pin, this glass is specifically selected for its ability to fuse to a 446 stainless steel pin, thereby avoiding the difficulties associated with welding molybdenum pins. The Jolson invention differs from the current invention in its use of a stainless steel conductor pin devoid of a metal sleeve sealed to the insulating glass.

Thus, it can be seen, based on a reading of the prior art, there is a need to develop a glass-to-metal seal suitable for providing a high strength terminal connection to a current collector as well as providing a hermetic seal for an electrochemical cell. This invention will extend the applicability of the current electrochemical cells to new varieties of applications. This design is less cumbersome and more adaptable than others heretofore presented.

SUMMARY OF THE INVENTION

Roughening the terminal pin helps bolster the connection with the current collector. However, this same roughening detracts from the integrity of the glass-to-metal seal. According to the present invention, it has been discovered that the glass-to-metal seal of electrochemical cells containing a current collector and a roughened terminal pin, such as of titanium, stainless steel, or molybdenum, can be improved by positioning a sleeve or couple over that portion of the terminal pin that will be sealed to the insulating glass. The present construction includes hermetically welding the sleeve or couple at each end of the terminal pin, and forming a glass-to-metal seal incorporating the modified terminal pin, the insulating glass, and the metallic lid. The resulting assembly contains a portion of the terminal pin that has a roughened surface and is suitable for making a high strength connection to a current collector and another portion which has a relatively smooth surface which provides high strength for a glass-to-metal seal.

The foregoing and additional advantages and characterizing features of the present invention will become clearly apparent upon reading the ensuing description together with the included drawings wherein:

BEST MODE FOR CARRYING OUT THE INVENTION

Figure 1:
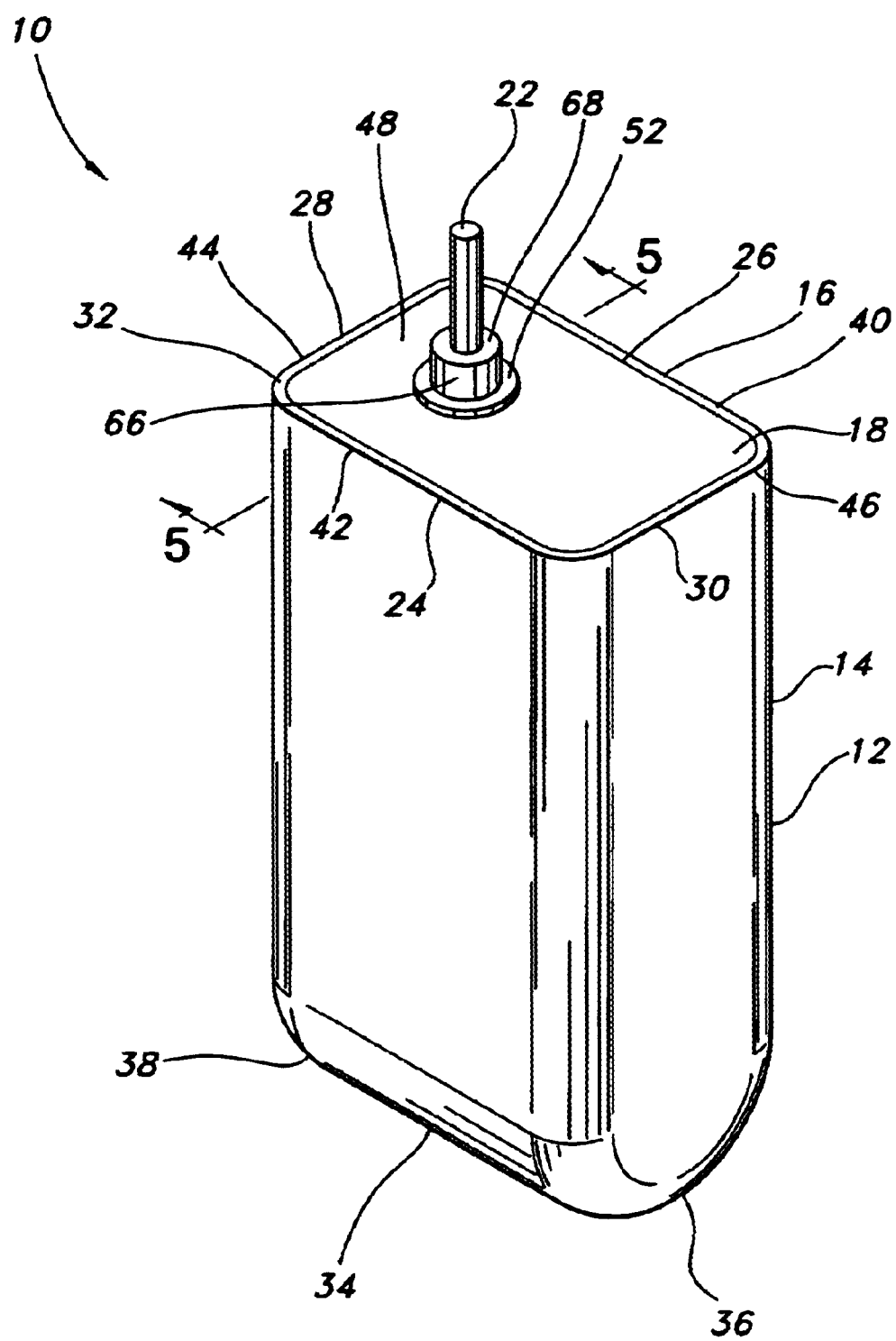
FIG. 1 is a perspective view of an electrochemical cell containing the new glass-to-metal seal.

Referring now to FIGS. 1 through 5, electrochemical cell 10 is similar to the prismatic electrochemical cell as described in U.S. Pat. No. 5,250,373 to Muffoletto et al. This patent is assigned to the assignee of the current invention and the disclosure of which is incorporated herein by reference.

In an embodiment of the current invention, the art has known that it has been difficult to weld an aluminum current collector to a high ferritic stainless steel or molybdenum terminal pin. Aluminum is stable as a current collector material when it is used in conjunction with a lithium hexafluorophosphate salt. Indeed, it is known that lithium/silver vanadium oxide batteries containing an aluminum current collector and a lithium hexafluoro-phosphate salt have increased power density in comparison to state-of-the-art batteries. This technology heretofore has not been used because of the molybdenum-aluminum welding problem.

However, according to the present invention, roughening the surface on a portion of the terminal pin followed by crimping and laser welding of the pin to the aluminum current collector results in greater mechanical strength. This new terminal pin construction is adaptable for cells having a wide variety of electrode configurations including prismatic, jellyroll, serpentine, button shape, and the like. For illustration purposes, the present invention will first be described with respect to a prismatic cell, as shown in FIGS. 1 to 5, and then a jellyroll cell, as shown in FIG. 6. This is by way of illustration only, and those skilled in the art will readily understand other cell configurations useful with the present invention.

The prismatic cell includes a casing 12 of two parts, a first part or body 14 and a second part or lid 16. In particular, the body 14 is generally rectangular in shape, consisting of spaced apart side walls 24 and 26 extending to and meeting with a first end wall 28 at rounded corners, further extending to and meeting with a second end wall 30 at rounded corners. The side walls 24 and 26, and end walls 28 and 30 extend to a continuous upper edge 32 defining an opening 18 of the body 14 opposite to the lower end. Side walls 24 and 26 further extending down and meet, forming a smooth arcuate surface 34. End walls 28 and 30 further extend downward and meet arcuate surface 34 with rounded ends 36 and 38. Rounded ends 36 and 38 are perpendicular to arcuate surface 34.

The lid 16 is a one piece member having spaced apart side walls 40 and 42 extending to and meeting with first end wall 44 at rounded corners, further extending to and meeting with a second end wall 46 with rounded corners. Side walls 40 and 42 and end walls 44 and 46 extend to and meet with upper surface 48, and further extend to and meet with lower surface 50. The lid 16 is sized just to fit within the upper opening 18 in the case body 14. The lid 16 is provided with an opening 52, used for a hermetically sealed battery terminal feedthrough 54, containing a terminal lead 22 with a glass-to-metal seal 56. The terminal lead will be described in detail later.

The lid 16 is received in a close proximate relationship inside the opening 18 of the body 14 and welded to provide a hermetic enclosure for an electrode assembly 20. The preferred methods of sealing the casing are welding and brazing. Casing 12 is of a conductive material preferably selected from the group consisting of nickel, aluminum, stainless steel, mild steel and titanium. An external cell electrical connection is provided by the terminal lead 22 and by a contact region comprising the lid 16 or entire conductive casing 12, which is insulated from the terminal lead 22, to prevent shorting.

Figure 2:
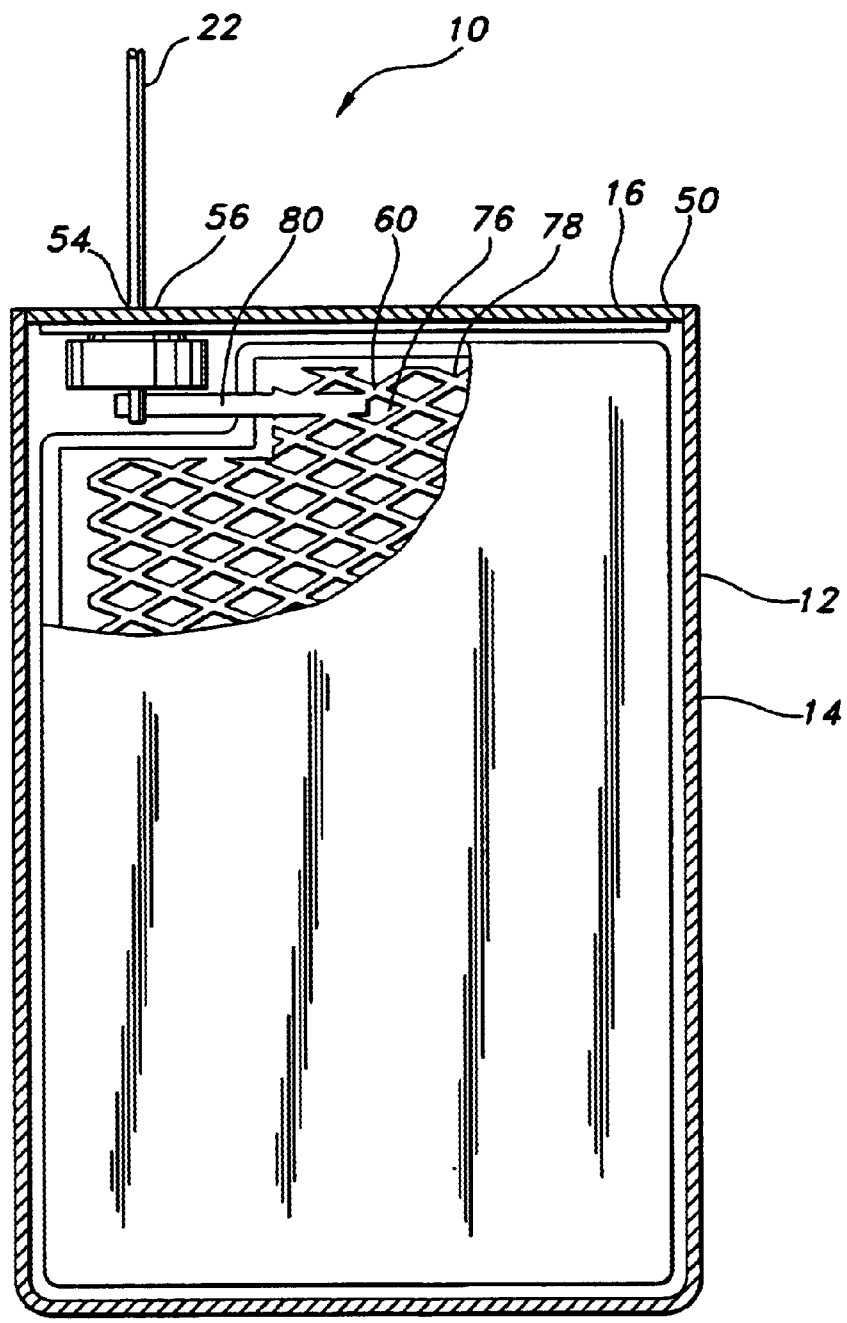
FIG. 2 shows a perspective view with parts broken away of the standard glass-to-metal seal showing the cathode connector attached to the terminal lead.
Figure 3A:
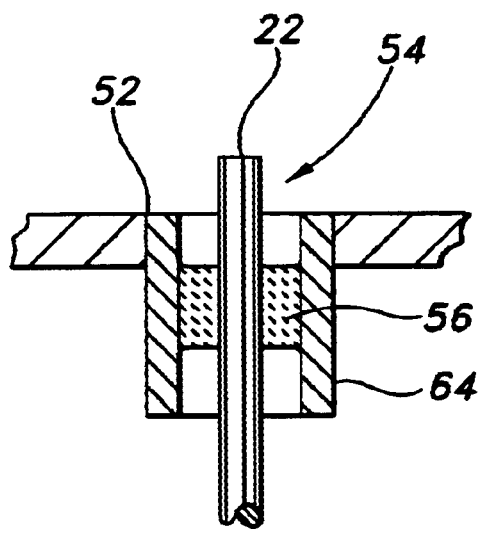
FIG. 3A is a detailed view of a prior art glass-to-metal seal.
Figure 3B:
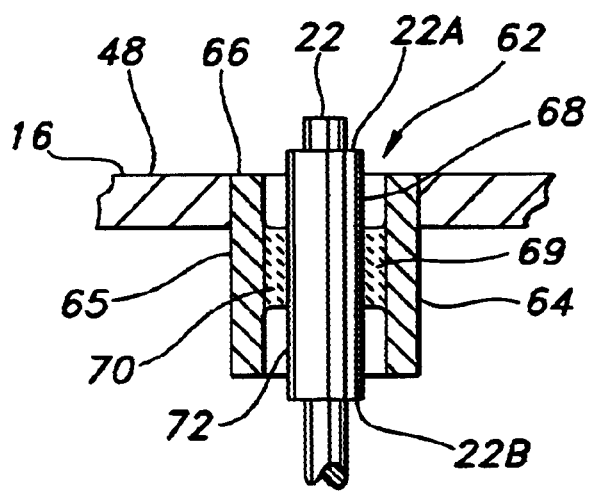
FIG. 3B is a detailed view of a glass-to-metal seal according to the present invention showing a sleeve surrounding the terminal pin and with the sealing glass contacting the sleeve.
Figure 4:
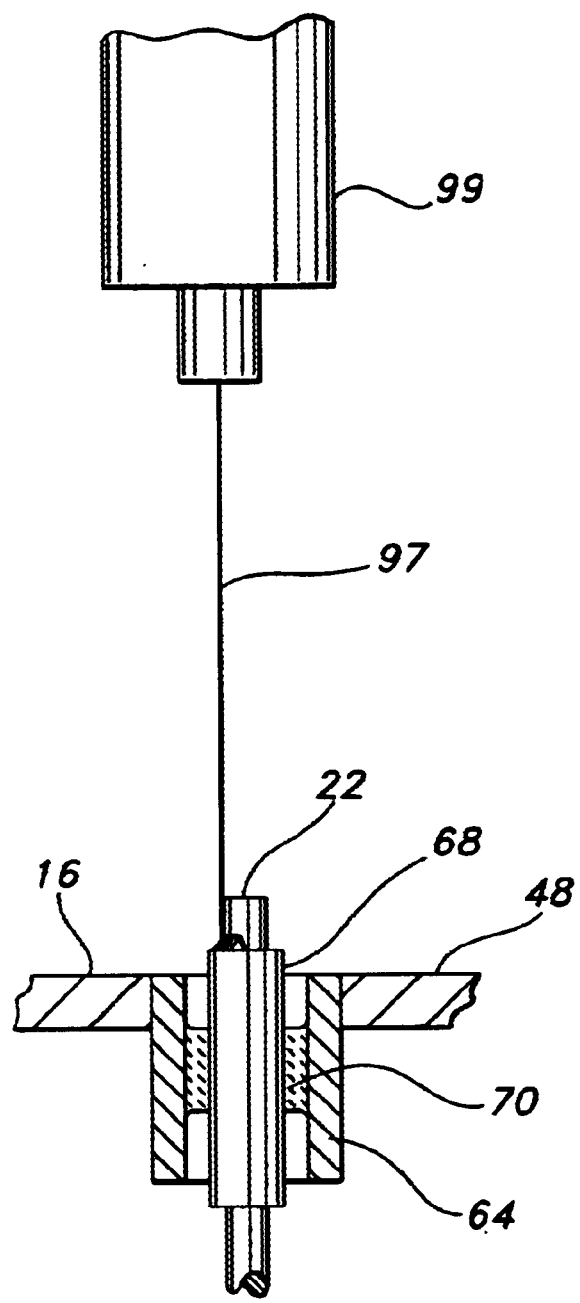
FIG. 4 is a detailed view showing the terminal pin connected to the sleeve by welding.

The feedthrough assembly 54 including a ferrule 64 and the glass-to-metal seal 56, is shown in FIGS. 2 and 3A. In this embodiment, the conventional seal, which has been used in many current applications, employs a high ferritic stainless steel or molybdenum terminal pin 22. In general, as previously stated, the pin is very difficult to weld to a current collector 60 (FIG. 2). However, the high ferritic stainless steel or molybdenum pin is highly thought of for its corrosion resistance capability. Thus, to enhance the use of the high ferritic stainless steel or molybdenum pin, a new terminal feedthrough 62, as shown in FIG. 3B, has been developed. The feedthrough consists of a ferrule 64 nested in an aperture 66 and attached to the lid 16 of the battery case. A generally cylindrical sleeve 68 of constant radius is disposed within the ferrule 64, parallel to the wall 65 of the ferrule 64, and perpendicular to the top surface 48 of lid 16. Sleeve 68 is sealed in the ferrule 64 by fusing the glass 69 between the sleeve 68 and the ferrule 64. The smooth outer surface 72 of the sleeve enhances the strength of the glass to metal bond. The high ferritic stainless steel or molybdenum pin 22 is abraded creating a rough surface, inserted through the sleeve and welded therein (FIG. 4). Sleeve 68 is welded to terminal pin 22 by using a laser beam 97 from welding source 99. Preferably, the sleeve 68 is welded about its entire peripheral extent to the pin 22 at both its upper and lower ends 22A and 22B. This creates a hermetical seal between the pin 22 and sleeve 68.

Sleeve 68 may or may not be of the same material as the terminal pin 22, however this is not a requirement as long as the two metals selected are capable of being welded together and are resistant to corrosion. Appropriate materials for the terminal pin include molybdenum, stainless steel, high ferritic stainless steel, titanium, niobium, and tantalum.

Figure 5:
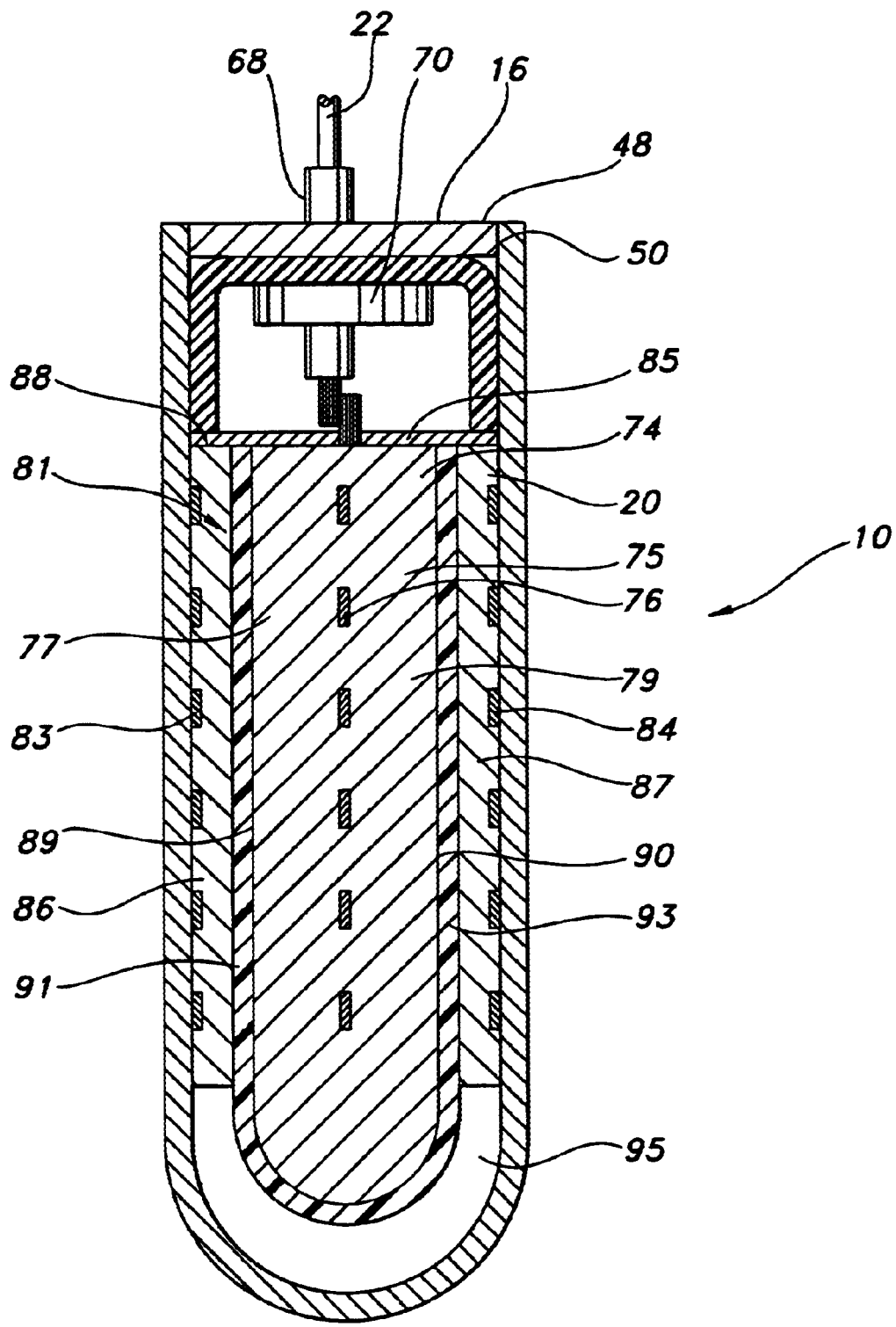
FIG. 5 is a sectional view along line 5—5 in FIG. 1, depicting the internals of an electrochemical cell.
Figure 6:
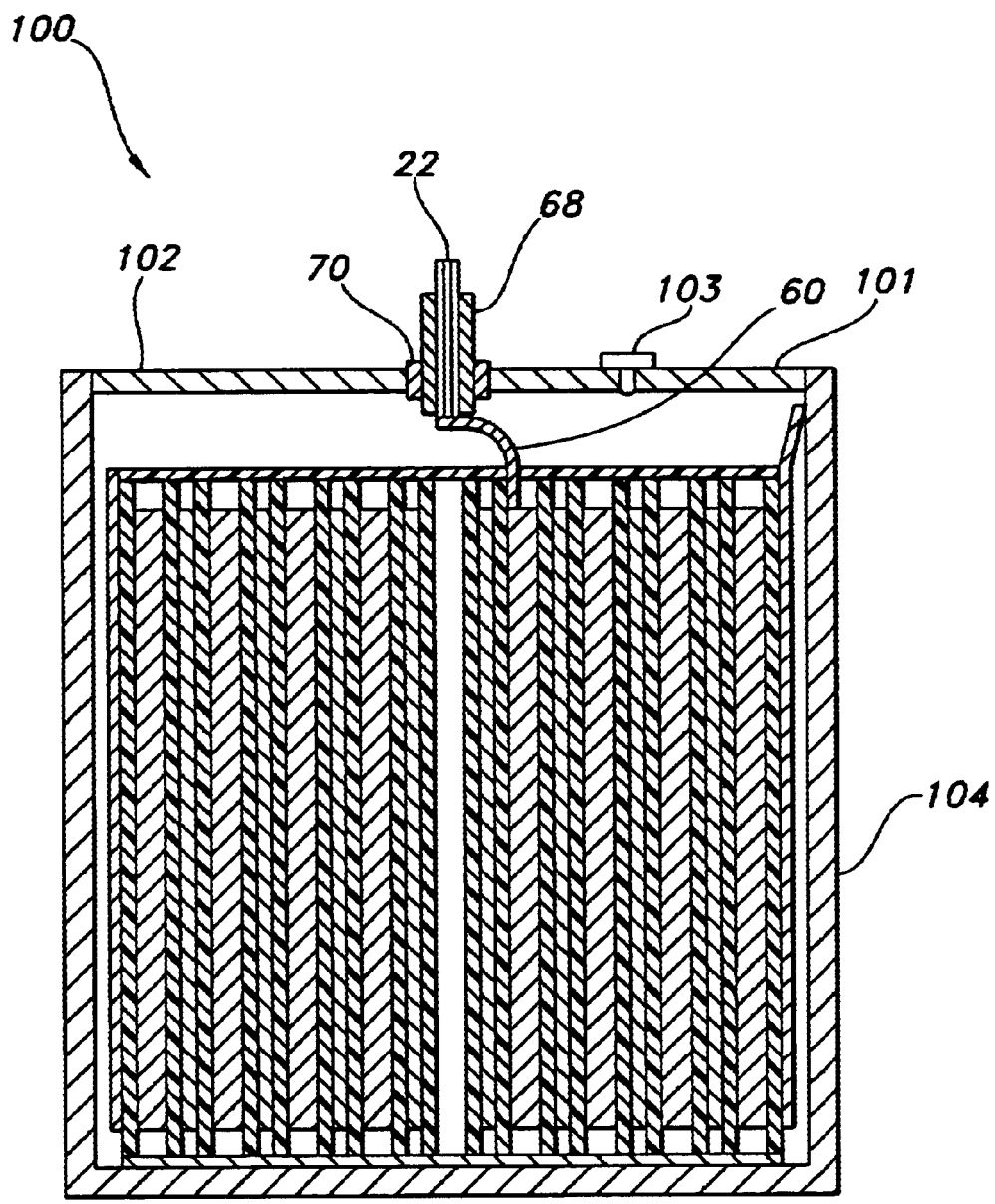
FIG. 6 shows a jellyroll electrode configuration using a glass-to-metal seal with sleeve according to the present invention.

As shown in FIGS. 2 and 5, the cell 10 further includes anode and cathode electrodes. The cathode 74 includes current collector 76. Current collector 76 generally comprises a grid 78, connected to a connection tab 80. A terminal lead 22 is directly contacted to the connection tab 80 preferably by welding, to provide for direct electrical connection to the cathode electrode. The current collector 76 is readily incorporated into alkali metal/solid cathode or alkali metal/oxyhalide electrochemical cells of both solid cathode and liquid electrolyte types without having to be changed or otherwise modified itself. In the solid cathode type, for example a lithium-solid cathode cell, a solid cathode material such as manganese dioxide, silver vanadium oxide, copper silver vanadium oxide, titanium disulfide, copper oxide, copper sulfide, iron sulfide, iron disulfide, carbon or fluorinated carbon ($CF_x$) is contained within casing 12 and surrounded by a separator. A preferred lithium anode 82 also is in the casing.

In the liquid cathode/electrolyte or catholyte type cell, for example a lithium-oxyhalide cell, liquid catholyte fills the casing interior and is in operative contact with the anode and with the cathode element comprising the cathode current collector 76 sandwiched between opposed carbonaceous plates. A separator is disposed between the anode and the carbonaceous cathode. For a more detailed description of such a liquid electrolyte cell references may be made to U.S. Pat. No. 4,246,327 to Skarstad et al.

The current invention may also be used in a secondary lithium cell. The secondary electrochemical cell which can be used with the present invention includes an anode active material selected from Groups IA, IIA, or IIIB of the Periodic Table of Elements, including the alkali metals lithium, sodium, potassium, etc.

In secondary electrochemical systems, the anode electrode comprises a material capable of intercalating and de-intercalating the alkali metal, and preferably lithium. A carbonaceous anode comprising any of the various forms of carbon (e.g., coke, graphite, acetylene black, carbon black, glassy carbon, etc.) which are capable of reversibly retaining the lithium species, is preferred. Graphite is particularly preferred due to its relatively high lithium-retention capacity. Regardless of the form of the carbon, fibers of the carbonaceous material are particularly advantageous because the fibers have excellent mechanical properties which permit them to be fabricated into rigid electrodes that are capable of withstanding degradation during repeated charge/discharge cycling. Moreover, the high surface area of carbon fibers allows for rapid charge/discharge rates. A preferred carbonaceous material for the anode of a secondary electrochemical cell is described in U.S. Pat. No. 5,443,928 to Takeuchi et al., which is assigned to the assignee of the present invention and incorporated herein by reference.

A typical secondary cell anode is fabricated by mixing about 90 to 97 weight percent graphite with about 3 to 10 weight percent of a binder material which is preferably a fluro-resin powder such as polytetrafluoroethylene (PTFE), polyvinylidene fluoride (PVDF), polyethylenetetrafluoroethylene (ETFE), polyamides and polyamides, and mixtures thereof. This electrode active admixture is provided on a current collector such as of a nickel, stainless steel, or copper foil or screen by casting, pressing, rolling or otherwise contacting the active admixture thereto.

The anode component further has an extended tab or lead of the same material as the anode current collector, i.e., preferably nickel, integrally formed therewith such as by welding and contacted by a weld to a cell case of conductive metal in a case-negative electrical configuration. Alternatively, the carbonaceous anode may be formed in some other geometry, such as a bobbin shape, cylinder or pellet to allow an alternate low surface cell design.

The cathode of a secondary cell preferably comprises a lithiated material that is stable in air and readily handled. Examples of such air-stable lithiated cathode materials include oxides, sulfides, selenides, and tellurides of such metals as vanadium, titanium, chromium, copper, molybdenum, niobium, iron, nickel, cobalt and manganese. The more preferred oxides include $LiNiO_2$, $LiMn_2O_4$, $LiCoO_{2.92}Sn_{0.08}O_2$, $LiCo_{1-x}Ni_xO_2$ and $LiCoO_2$.

Before fabrication into an electrode for incorporation into an electrochemical cell, the lithiated active material is preferably mixed with a conducted additive. Suitable conductive additives include acetylene black, carbon black and/or graphite. Metals such as nickel, aluminum, titanium and stainless steel in powder form are also useful as conductive dilutants when mixed with the above listed active materials. The electrode further comprises a fluoro-resin binder, preferably in a powder form, such as PTFE, PVDF, ETFE, polyamides and polyimides, and mixtures thereof.

To recharge such secondary cells, the lithium ion comprising the cathode is intercalated into the carbonaceous anode by applying an externally generated electrical potential to recharge the cell. The applied recharging electrical potential serves to draw the alkali metal ions from the cathode material, through the electrolyte and into the carbonaceous anode to saturate the carbon comprising the anode. The resulting $Li_xC_6$ electrode can have an x ranging between 0.1 and 1.0. The cell is then provided with an electrical potential and is discharged in a normal manner.

An alternate secondary cell construction comprises intercalating the carbonaceous material with the active alkali material before the anode is incorporated into the cell. In this case, the cathode body can be solid and comprise, but not be limited to, such materials as manganese dioxide, silver vanadium oxide, copper silver vanadium oxide, titanium disulfide, copper oxide, copper sulfide, iron sulfide, iron disulfide, carbon and fluorinated carbon. However, this approach is compromised by the problems associated with handling lithiated carbon outside of the cell. Lithiated carbon tends to react when contacted by air.

The secondary cell used in the present invention includes a separator to provide physical segregation between the anode and cathode active electrodes. The separator is of an electrically insulative material to prevent an internal electrical short circuit between the electrodes, and the separator material also is chemically unreactive with the anode and cathode active materials and both chemically unreactive with and insoluble in the electrolyte. In addition, the separator material has a degree of porosity sufficient to allow flow therethrough of the electrolyte during the electrochemical reaction of the cell. The form of the separator typically is a sheet which is placed between the anode and cathode electrodes. Such is the case when the anode is folded in a serpentine-like structure (not shown) with a plurality of cathode plates disposed intermediate the anode folds and received in a cell casing or when the electrode combination is rolled or otherwise formed into a cylindrical "jellyroll" configuration, as shown per FIG. 6.

Illustrative separator materials include fabrics woven from fluoropolymeric fibers of polyethylenetetrafluoroethylene and polyethylenechlorotrifluoroethylene used either alone or laminated with a fluoropolymeric microporous film. Other suitable separator materials include non-woven glass, polypropyene, polyethylene, glass fiber materials, ceramics, a polytetraflouroethylene membrane commercially available under the designation ZITEX (Chemplast Inc.), a polypropylene membrane commercially available under the designation CELGARD (Celanese Plastic Company, Inc.) and a membrane commercially available under the designation DESIGLAS (C. H. Dexter, Div., Dexter Corp.).

Referring now to FIG. 5, the primary cell 10, according to a second embodiment of the present invention, is of the liquid electrolyte type comprising a cathode electrode 74 having a body 75 of solid cathode material in the form of plates 77, 79 pressed together and bonded against the cathode current collector 76. The cathode active material is preferably comprised of a metal, a metal oxide, a mixed metal oxide or a metal sulfide, and the cathode current collector 76 is fabricated from a thin sheet of metal selected from the group consisting of nickel, aluminum, stainless steel, mild steel and titanium, with titanium being preferred.

As further shown in FIG. 5, cell 10 includes an alkali metal anode electrode, generally designated 81, comprising a unitary, conductive member which serves as the anode current collector and is fabricated from a thin sheet of metal, preferably nickel, having a pair of wing-like sections 83 and 84 joined by an intermediate web section 85. The preferred alkali metal for the anode is lithium. Lithium anode elements 86 and 87 are in pressure bonded contact with and carried by corresponding ones of the electrode wing sections 83 and 84, respectively. The wing-like sections 83 and 84 are of mesh formation to facilitate adherence to the lithium anode elements 86, 87. The lithium anode elements 86 and 87 are of similar shape or configuration as the corresponding electrode wing sections 83 and 84, respectively, but of a slightly larger size or surface area so as to define a marginal or peripheral extension or border surrounding the perimeter of each wing section. Thus, the length and width of each of the lithium anode elements 86 and 87 is slightly greater than the length and width of the corresponding electrode wing section 83 and 84 with the anode elements terminating at an edge 88 a short distance from electrode web section 85.

To construct an anode-cathode subassembly according to the present invention, the electrode wing sections 83, 84 with the associated anode lithium elements 86, 87 are folded relative to web section 85 and toward each other and in a manner to place the lithium anode elements 86, 87 in operative contact with the oppositely directed surfaces 89 and 90 of the cathode body 75. In particular, lithium anode element 86 is in operative contact with the cathode body surface 89 through a thin sheet of separator material 91. Similarly, lithium anode element 87 is in operative contact with cathode body surface 90 through a thin sheet of separator material 93 such that separator sheets 91 and 93 surround and envelope the cathode body 75 to prevent direct physical contact with the anode plates 86, 87. Shielding and insulating sheets (not shown) are also provided between the web section 85 of the anode current collector and the cathode electrode 74. The terminal lead 22 connected to the current collector 60 of the cathode electrode 74 extends through a header assembly comprising the glass-to-metal seal 70 fitted in the lid 16 (FIGS. 3B and 5).

Cell 10 is completed by a liquid electrolyte 95 provided in casing 12 and sealed therein by the provision of a closure means to hermetically close the cell 10. Lead 22 is the positive electrical terminal, being connected to the cathode body 75. With anode electrode 82 being in operative contact with the conducting casing 12 through the web section 85 of the anode current collector in electrical contact therewith, the cell 10 of this embodiment of the present invention is in a case-negative electrical configuration.

By way of example, in an illustrative cell, the active material of cathode body 75 is a silver vanadium oxide cathode material as described in U.S. Pat. Nos. 4,310,609 and 4,391,729 to Liang et al., or copper silver vanadium oxide as described in U.S. Pat. Nos. 5,472,810 and 5,516,340 to Takeuchi et al., all assigned to the assignee of the present invention, the disclosures of which are hereby incorporated by reference. Cathode current collector 76 is of titanium and terminal lead 22 is of molybdenum, separators 91, 93 are of polypropylene, electrolyte 95 is a 1.0M to 1.4M solution of $LiAsF_6$ or $LiPF_6$ in a 50:50 mixture of, by volume, 1,2-dimethoxyethane and propylene carbonate, and glass seal 70 is of TA-23 Hermetic sealing glass, and the metal plug of the closure means is of stainless steel.

The current collector 76 of the present invention can also be employed in a cell having a case-positive electrical configuration. In particular, in the embodiments of FIGS. 2 and 5, with the lithium anode elements 86, 87 contacting the conductive cell casing 12, the cell 10 is in a case-negative electrical configuration. A case-positive electrical configuration is provided by placing the cathode parts in contact with the conductive cell casing 12. In particular, and referring to the anode-cathode subassembly of FIG. 5, a case-positive electrical configuration is provided by replacing lithium anode elements 86, 87 with cathode plates 77, 78 on the electrode wing sections 83, 84. Accordingly, cathode body 75 would be replaced by a pair of lithium anode elements 86, 87 sandwiched together and against the current collector 76 of the present invention serving as an anode current collector which, in turn, is connected to the terminal lead 22 via electrical contact with the collector 76, and insulated from lid 16 by the glass-to-metal seal 70. With the cathode parts in contact with electrode wing sections 83, 84 and with the electrode web section 85 in contact with the cell casing 12, a cell is provided in a case-positive electrical configuration. In all other respects, the anode current collector in the case-positive configuration is similar to that previously described with respect to cell 10 having the case-negative configuration.

In the current invention, the novel glass-to-metal seal 70 has been discussed in conjunction with a prismatic casing 12. However, as previously described, this is for illustrative purposes only. As those who are skilled in the art can appreciate, the novel glass-to-metal seal is useful with any casing design which allows access to the external or internal surface of the terminal lead, depending on the desired design. The available designs include clam shell, prismatic, cylindrical, or button shapes. It may also be used with a number of different types of batteries including primary lithium batteries, implantable batteries, lithium based rechargeable cells and also acid or alkaline based batteries.

For example, FIG. 6 shows another embodiment of the present invention having a jellyroll electrode assembly 100. One of the anode electrodes and the cathodes electrode of the jellyroll assembly contains a current collector 60 attached to terminal pin 22 extending above the lid 102 for the casing 101. The terminal pin 22 extends through the sleeve 68 sealed in an opening in the lid by the glass-to-metal seal 70. The battery further contains a fill opening 101 sealed by plug 103.

Now, it is therefore apparent that the present invention accomplishes its intended objects. While embodiments of the present invention have been described in detail, which is for the purpose of illustration, not limitation.

We claim:
1. An electrochemical cell, comprising:
    a) a casing of electrically conductive material having an open end;
    b) a first and a second electrodes having a separator disposed therebetween inside the casing in electrical association with each other, wherein at least one of the electrodes includes a current collector;
    c) an electrolyte activating the first and the second electrodes;
    d) a lid of electrically conductive material closing the open end of the casing;
    e) a terminal lead having a first terminal lead end disposed inside the casing connected to the current collector and a second terminal lead end disposed outside the casing for connection to a load; and
    f) a sleeve sealed in a lid opening and comprising a sleeve opening extending to first and second sleeve ends, wherein the terminal lead is received in the sleeve opening with the first sleeve end sealed to the terminal lead proximate the first terminal lead end and the second sleeve end sealed to the terminal lead proximate the second terminal lead end.

2. The electrochemical cell of claim 1 wherein the sleeve is isolated from the casing by a glass-to-metal seal.

3. The electrochemical cell of claim 1 wherein the terminal lead has at least a portion of its surface roughened.

4. The electrochemical cell of claim 1 wherein the sleeve and the terminal lead are made from at least one of the group consisting of molybdenum, stainless steel, high ferritic stainless steel, titanium, niobium, and tantalum.

5. The electrochemical cell of claim 1, wherein the terminal lead is attached to the sleeve by welding.

6. The electrochemical cell of claim 1 wherein the first and second electrodes are electrically associated in either a jellyroll configuration or a prismatic configuration.

7. The electrochemical cell of claim 1, as a primary cell.

8. The electrochemical cell of claim 1, as a secondary cell.

9. The electrochemical cell of claim 1, associated with an implantable medical device powered by the cell.

10. An electrochemical cell, comprising:
   a) a casing of electrically conductive material;
   b) an anode and a cathode housed inside the casing and having a separator disposed therebetween, wherein the anode is of lithium and the cathode comprises silver vanadium oxide contacted to a current collector;
   c) an electrolyte activating the anode and the cathode;
   d) a lid of electrically conductive material closing the open end of the casing;
   e) a terminal lead having at least a portion of its surface roughened, wherein a first terminal lead end is disposed inside the casing connected to the current collector and a second terminal lead end is disposed outside the casing for connection to a load; and
   f) a sleeve sealed in a lid opening and comprising a sleeve opening extending to first and second sleeve ends, wherein the terminal lead is received in the sleeve opening with the first sleeve end sealed to the terminal lead proximate the first terminal lead end and the second sleeve end sealed to the terminal lead proximate the second lead end.

11. The electrochemical cell of claim 10 wherein the sleeve is isolated from the casing by a glass-to-metal seal.

12. The electrochemical cell of claim 10 wherein the conductive sleeve is attached to the terminal lead by welding.

13. An electrochemical cell, which comprises:
   a) an anode comprising lithium;
   b) a cathode of at least one cathode active material selected from the group consisting of manganese dioxide, silver vanadium oxide, copper silver vanadium oxide, titanium disulfide, copper oxide, copper sulfide, iron sulfide, iron disulfide, carbon, and fluorinated carbon ($CF_x$), wherein at least one of the anode and the cathode includes a current collector;
   c) an electrolyte activating the anode and the cathode having a separator disposed therebetween and housed in an electrical association with each other in a casing having an open end;
   d) a lid of electrically conductive material closing the open end of the casing;
   e) a terminal lead having a first terminal lead end disposed inside the casing connected to the current collector and a second terminal lead end disposed outside the casing for connection to a load; and
   f) a sleeve sealed in the lid opening and comprising a sleeve opening extending to first and second sleeve ends, wherein the terminal lead is received in the sleeve opening with the first sleeve end sealed to the terminal lead proximate the first terminal lead end and the second sleeve end sealed to the terminal lead proximate the second terminal lead end.

14. A method for providing an electrochemical cell, comprising the steps of:
   a) providing a casing of electrically conductive material having an open end;
   b) providing a first and a second electrodes having a separator disposed therebetween inside the casing in electrical association with each other, wherein at least one of the electrodes includes a current collector;
   c) providing an electrolyte activating the first and the second electrodes;
   d) providing a lid of electrically conductive material having an opening therein, the lid closing the open end of the casing;
   e) providing a terminal lead, having a first terminal lead end and a second terminal lead end;
   f) providing a sleeve comprising a sleeve opening extending to first and second sleeve ends;
   g) positioning the terminal lead in the sleeve opening and sealing the first sleeve end to the terminal lead proximate the first terminal lead end and the second sleeve end to the terminal lead proximate the second terminal lead end; and
   h) sealing the sleeve in the lid opening with the first terminal lead end connected to the current collector inside the casing and the second terminal lead end disposed outside the casing for connection to a load.

15. The method of claim 14 including roughening at least a portion of the terminal lead before sealing it to the sleeve.

16. The method of claim 14 including sealing the sleeve in the lid opening isolated from the casing by a glass-to-metal seal.

17. The method of claim 14, including providing the sleeve and the terminal lead made from at least one of the group consisting of molybdenum, stainless steel, high ferritic stainless steel, titanium, niobium and tantalum.

18. The method of claim 14, including welding the terminal lead to the metal sleeve.

19. The method of claim 14 including providing the first and the second electrodes in electrical association with each other in either a jellyroll configuration or a prismatic configuration.

20. The method of claim 14 including using the electrochemical cell to power an implantable medical device.

* * * * *

UNITED STATES PATENT AND TRADEMARK OFFICE
CERTIFICATE OF CORRECTION

PATENT NO.    : 6,670,074 B2
DATED         : December 30, 2003
INVENTOR(S)   : Spillman It is certified that error appears in the above-identified patent and that said Letters Patent is hereby corrected as shown below:

<u>Title page, Item [54] and Column 1, line 1,</u>
Title, "GLASS TO METAL SEAL" should be -- GLASS TO METAL SEAL FOR AN ELECTROCHEMICAL CELL --.

Signed and Sealed this

Eighteenth Day of October, 2005

JON W. DUDAS
*Director of the United States Patent and Trademark Office*